United States Patent [19]

Tapolyai

[11] Patent Number: 4,782,093
[45] Date of Patent: Nov. 1, 1988

[54] METHOD OF TREATING EPILEPSY AND CEREBRAL CONCUSSION

[76] Inventor: Mihaly A. Tapolyai, 3643 Lindholm Rd., Cleveland, Ohio 44120

[21] Appl. No.: 55,456

[22] Filed: May 28, 1987

[51] Int. Cl.$^4$ ............................................. A61K 31/135
[52] U.S. Cl. .................................... 514/649; 514/653
[58] Field of Search ................................. 514/649, 653

Primary Examiner—Stanley J. Friedman
Attorney, Agent, or Firm—Frost & Jacobs

[57] ABSTRACT

A method for treatment of epilepsy and cerebral concussion in mammals by administration of a vasodilator in an effective amount, the vasodilator being bamethan, derivatives thereof, bamethan sulfate, derivatives thereof, l-epinephrine derivatives having a terminal alkyl substitutent attached to nitrogen and containing at least three carbon atoms, and mixtures thereof. The frequency of epileptic seizures in mammalian patients is substantially reduced by this treatment.

10 Claims, 2 Drawing Sheets

METHOD OF TREATING EPILEPSY AND CEREBRAL CONCUSSION

BACKGROUND OF THE INVENTION

This invention relates to a method for treatment of epilepsy of any type and cerebral concussion in mammals by administration of a vasodilator chosen from the group consisting of bamethan, derivatives thereof, bamethan sulfate, derivatives thereof, 1-epinephrine derivatives having a terminal alkyl substituent attached to nitrogen and containing at least three carbon atoms, and mixtures thereof. More specifically, the method of the present invention has been found to have great utility in decreasing the frequency of epileptic seizures in mammalian patients afflicted with epilepsy of vascular origin.

The most prevalent form of epilepsy of vascular origin is *Uncus sclerosis*, or a type of temporal lobe epilepsy. It has been hypothesized that compression of the branches of the anterior choroid artery against the free edge of the tentorium cerebelli at birth is responsible for lesions which are the cause of a type of temporal epilepsy. Applicant conceived a treatment based on the assumption that a vasodilator might improve the nutrition and oxygenization of the lesion which causes such epileptic seizures. However, tests by applicant with several well known vasodilators, under control of an electroencephalogram, were found to have no effect. More specifically, known vasodilators which proved to be ineffective were papaverine, theophylline, niacin (nicotinic acid), and complamin.

In contrast, tests by applicant with bamethan sulfate were found to have a surprising and significant effect in decreasing the frequency of epileptic seizures.

Conventional antiepileptic drugs include phenobarbital, hydantoin derivatives, primidone and tridione.

SUMMARY OF THE INVENTION

Compounds similar to epinephrine but having an alkyl group attached to nitrogen containing a sufficient number of carbon atoms to cause vasodilation rather than vasoconstriction have been found to be effective in the practice of the present invention.

In accordance with the invention there is provided a method of treating epilepsy of any type and cerebral concussion in mammals, which comprises administering to an affected mammal an effective amount of a vasodilator chosen from the group consisting of bamethan, bamethan derivatives, bamethan sulfate, bamethan sulfate derivatives, 1-epinephrine derivatives having a terminal alkyl substitutent attached to nitrogen containing at least three carbon atoms, and mixtures thereof.

In a more specific use of the method of the invention, the frequency of epileptic seizures in mammalian patients afflicted with epilepsy of vascular origin has been markedly decreased.

BRIEF DESCRIPTION OF THE DRAWINGS

Reference is made to the accompanying drawings wherein.

DETAILED DESCRIPTION OF THE INVENTION

The generic structural formula of the vasodilator used in the method of the invention is as follows:

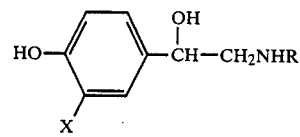

Derivatives of 1-epinephrine (adrenalin) wherein the terminal alkyl group (R) attached to nitrogen contains from 3 to 8 carbon atoms, and wherein X is hydrogen or hydroxyl, are effective in the present method. The 1-epinephrine native compound has a terminal methyl group attached to nitrogen, and this is believed to account for the alpha-adrenergic effect, so that 1-epinephrine acts as a vasoconstrictor. However, when the methyl group on epinephrine is substituted by an alkyl group containing from 3 to 8, preferably 4, carbon atoms, the adrenergic effect is weakened, and the affinity to the beta receptors increases. The effect then becomes one of vasodilation and anticonvulsive action. The upper limit on the number of carbon atoms is not critical and may exceed 8 if desired, but the lower limit of 3 carbon atoms should be observed.

Bamethan is a preferred compound in the practice of the method of the invention and has the following structural formula:

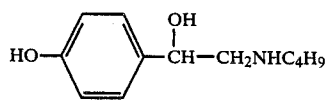

Bamethan has a terminal butyl group attached to nitrogen. This compound, or the sulfate salt thereof, is produced by a number of companies under product names such as Vasculate, Vaskulit, Vaskunicol, Rotesar, Butedrin, Bupatol and Garmian. Bamethan is also known as Butyl-Nor-Sympatol.

The hypothetical cause of epilepsy of vascular origin has been set forth above. A form of epilepsy known as Status Epilepticus is a state in which attacks occur in rapid succession without recovery of consciousness. This may be of vascular origin. This form can also be treated in accordance with the present method. Cerebral concussion of a severity which may have lasting effect is also believed to respond to the present treatment.

Figure 1:
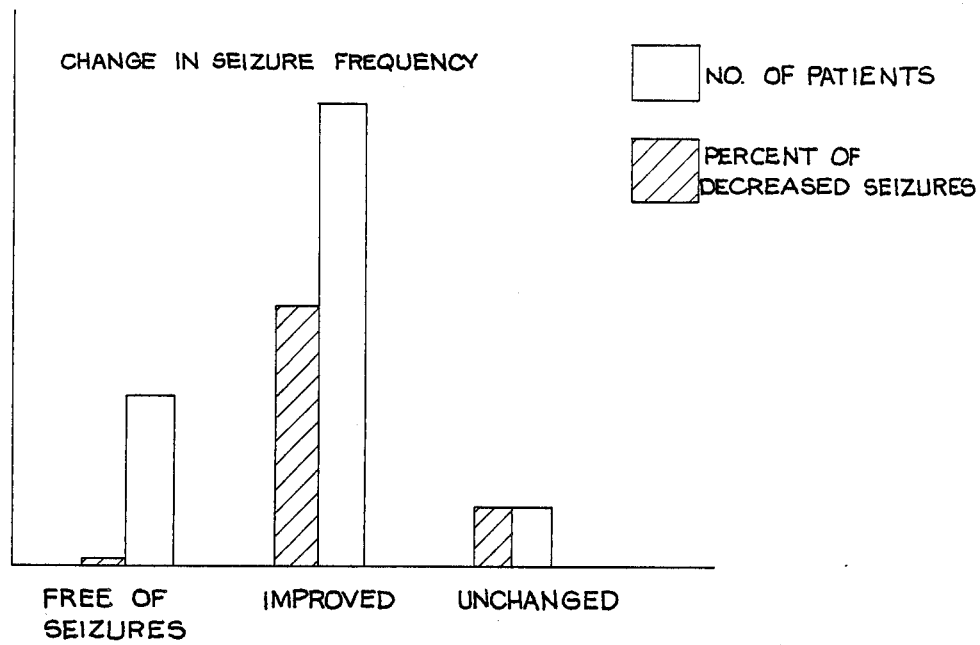
FIG. 1 is a bar graph illustrating the changes in seizure frequency resulting from the method of the invention.

Experimental studies conducted on numerous patients in a foreign country (Hungary) have verified the effectiveness of the method of the invention. Reference is made to FIG. 1, from which it is apparent that nearly 50% of patients treated with bamethan sulfate had a decreased frequency in seizures, a very small percentage became free of seizures, and about 12% to 13% were unchanged.

Figure 2:
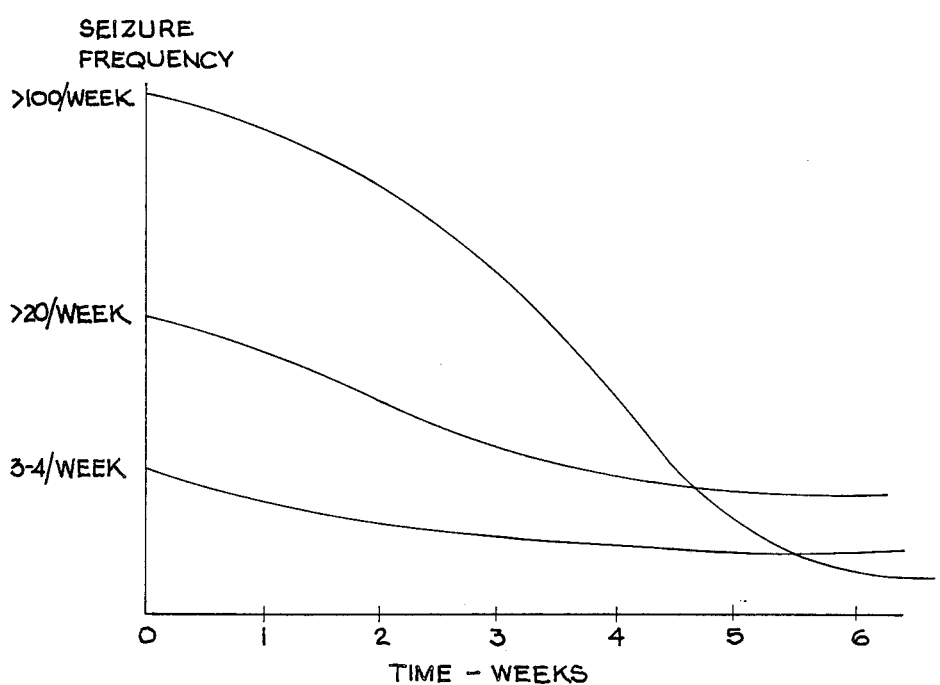
FIG. 2 is a graphic illustration of the correlation between seizure frequency with conventional antiepileptics and with the treatment of the invention.

FIG. 2 is a graphic representation of correlation between seizure frequency with conventional antiepileptic drugs and decrease in seizure frequency over a six week period of time, when treated with bamethan or bamethan sulfate. The basic seizure frequency at zero time on the graph of FIG. 2 was that existing with a conventional antiepileptic drug prescribed by a clinic and taken regularly, such as phenobarbital, hydantoin derivatives, primidone, tridione, etc. Treatment with bamethan sulfate was begun at zero time, and for the first three weeks the conventional antiepileptic drugs were also continued. After three weeks the conventional antiepileptic drugs were gradually tapered off or discontinued altogether, with bamethan sulfate treatment extended out to six weeks. In practice, such treatment would be continued for a minimum of two years, with the reduced seizure frequency shown at the six week stage in the graph of FIG. 2, in a stabilized state.

It is apparent from FIG. 2 that patients initially having a high number of seizures per week were greatly benefitted, and after six weeks displayed lower frequency of seizures than patients initially having much lower seizure frequencies. In all instances, however, improvement was significant.

Figure 3:
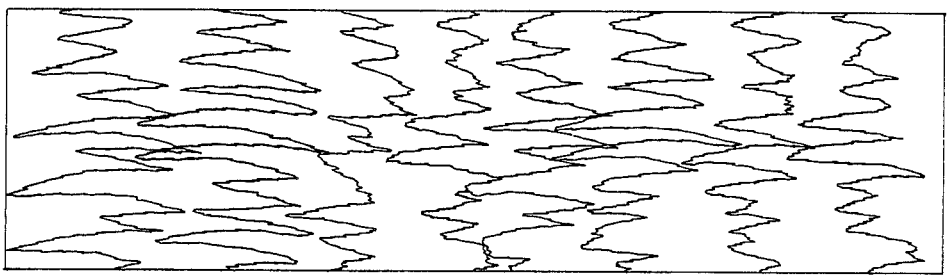
FIG. 3 illustrates electroencephalogram charts compared before and after the treatment of the invention.
Figure 3:
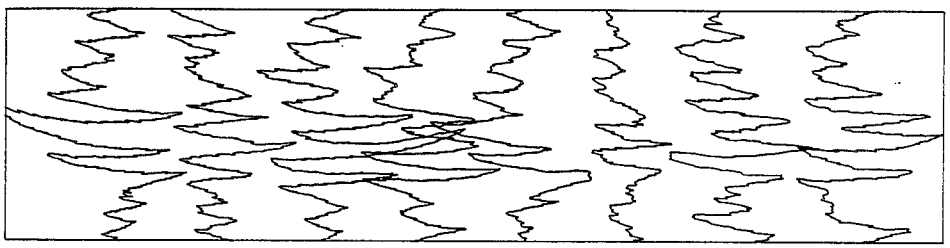

FIG. 3 is a representation of portions of EEG charts comparing patterns before and after intramuscular injection of bamethan sulfate. It will be apparent that some localization resulted from treatment.

An analysis of more than 60 cases on the basis of the region of lesion is set forth in the following table. This is in accordance with the Gibbs classification. It is apparent that improvement on average was about 50%.

TABLE

| Region: | Improved | Slightly Improved | No Change | Total | Rate |
|---|---|---|---|---|---|
| Focal | | | | | |
| Frontal | — | — | 5 | 5 | 7.2% |
| Temporal anterior | 18 | 4 | — | 22 | 31.8% |
| Mid-temporal | — | 3 | 1 | 4 | 7.2% |
| Diencephal | 3 | 2 | — | 5 | 7.2% |
| All improvements | 21 | 9 | | 30 | 53.4% |
| Diffuse | | | | | |
| Pure petit mal | 9 | 3 | — | 12 | 17.3% |
| Mixed petit mal | 6 | 1 | — | 7 | 10.1% |
| Myoclonic | — | 4 | — | 4 | 5.7% |
| Pure grand mal | 3 | 5 | — | 8 | 11.6% |
| Hyp- | — | 1 | 1 | 2 | 2.8% |

TABLE-continued

| Region: | Improved | Slightly Improved | No Change | Total | Rate |
|---|---|---|---|---|---|
| sarrhythmia | | | | | |
| All improvements | 18 | 14 | | 32 | 47.5% |

Regular treatment is administered orally by tablets containing 0.015 g bamethan sulfate, five times daily, for a person of average weight. Dosage ranges from 0.0003 to 0.0013 g per kilogram of body weight.

Treatment for Status epilepticus is effected by intramuscular injection, the dosage level being 1 to 2 ml of 1% solution twice in two hours.

I claim:

1. A method of treating epilepsy and cerebral concussion in mammals, which comprises administering to an affected mammal an effective amount of a vasodilator selected from the group consisting of bamethan, a bamethan derivative, bamethan sulfate, a bamethan sulfate derivative, a 1-epinephrine derivative having a terminal alkyl substitutent attached to nitrogen and containing at least three carbon atoms, and mixtures thereof.

2. A method of decreasing the frequency of epileptic seizures in mammalian patients afflicted with epilepsy of vascular origin, which comprises administering to an afflicted patient an effective amount of a vasodilator selected from the group consisting of bamethan, a bamethan derivative, bamethan sulfate, a bamethan sulfate derivative, a 1-epinephrine derivative having a terminal alkyl substitutent attached to nitrogen and containing a number of carbon atoms sufficient to prevent vasoconstriction and to cause vasodilation, and mixtures thereof.

3. The method of claim 1, wherein said alkyl substitutent contains from 3 to 8 carbon atoms.

4. The method of claim 3, wherein said alkyl substitutent contains 4 carbon atoms.

5. The method of claim 2, wherein said alkyl substitutent contains from 3 to 8 carbon atoms.

6. The method of claim 5, wherein said alkyl substitutent contains 4 carbon atoms.

7. The method of claim 1, wherein said vasodilator is at least one of bamethan and bamethan sulfate.

8. The method of claim 2, wherein said vasodilator is at least one of bamethan and bamethan sulfate.

9. The method of claim 1, wherein said vasodilator is administered orally.

10. The method of claim 2, wherein said vasodilator is administered by subcutaneous injection.

* * * * *